(12) United States Patent
Gofman et al.

(10) Patent No.: US 7,167,829 B2
(45) Date of Patent: Jan. 23, 2007

(54) CURING LAMP APPARATUS GIVING OPERATING CONDITIONS WITH ELECTRONIC VOICE

(75) Inventors: Igor Y Gofman, Croton-on-Hudson, NY (US); Joseph G. Colombo, Hackensack, NJ (US)

(73) Assignee: Coltene / Whaledent Inc., Cuyahoga Falls, OH (US)

( * ) Notice: Subject to any disclaimer, the term of this patent is extended or adjusted under 35 U.S.C. 154(b) by 239 days.

(21) Appl. No.: 10/273,395

(22) Filed: Oct. 17, 2002

(65) Prior Publication Data

US 2003/0071607 A1 Apr. 17, 2003

Related U.S. Application Data

(60) Provisional application No. 60/329,956, filed on Oct. 17, 2001.

(51) Int. Cl.
    *G10L 13/02* (2006.01)
(52) U.S. Cl. ..................................... 704/274
(58) Field of Classification Search ............. 704/200.1, 704/258, 260, 271, 274; 707/10; 362/573; 340/692; 433/228.1, 29; 369/22; 250/492.1, 250/227.24, 504.4; 315/91; 368/10; 422/186.3; 607/88
    See application file for complete search history.

(56) References Cited

U.S. PATENT DOCUMENTS

| | | | |
|---|---|---|---|
| 4,275,274 A * | 6/1981 | English .................... 369/22 |
| 4,298,806 A * | 11/1981 | Herold .................. 250/504 H |
| 4,412,099 A | 10/1983 | Niyada et al. |
| 4,450,139 A * | 5/1984 | Bussiere et al. ......... 422/186.3 |
| 4,785,420 A | 11/1988 | Little |
| 4,864,226 A * | 9/1989 | Tachimoto et al. ......... 324/157 |
| 4,961,028 A * | 10/1990 | Tanaka ....................... 315/91 |
| 4,968,252 A | 11/1990 | Creps |
| 5,097,136 A * | 3/1992 | Meyer et al. ............ 250/492.1 |
| 5,397,892 A * | 3/1995 | Abdelqader ............ 250/227.24 |
| 5,487,662 A | 1/1996 | Kipke et al. |
| 5,708,627 A * | 1/1998 | Gormley ...................... 368/10 |
| 5,879,159 A | 3/1999 | Cipolla |
| 6,068,485 A * | 5/2000 | Linebarger et al. ......... 704/271 |
| 6,089,740 A * | 7/2000 | Forehand et al. ........... 362/573 |
| 6,095,812 A * | 8/2000 | Senn et al. .................... 433/29 |
| 6,144,310 A * | 11/2000 | Morris ....................... 340/692 |
| 6,161,092 A | 12/2000 | Latshaw et al. |

(Continued)

FOREIGN PATENT DOCUMENTS

DE    34 47 639    7/1986

(Continued)

OTHER PUBLICATIONS

European Search Report dated Nov. 26, 2004.

*Primary Examiner*—Angela Armstrong
(74) *Attorney, Agent, or Firm*—Katten Muchin Rosenman LLP

(57) ABSTRACT

A curing lamp apparatus is used for providing electronic voice information to report a number of operating conditions associated with the curing lamp. The apparatus includes a light sensor for sensing output power, voltage and current sensors for sensing input power, a microcontroller for providing a digital number in response to receiving signals from one or more sensors, a programmed voice circuit for retrieving a voice message signal from a memory, address associated with the digital number, and a transducer for receiving and audibly reproducing the voice message signal.

8 Claims, 3 Drawing Sheets

U.S. PATENT DOCUMENTS

| | | | |
|---|---|---|---|
| 6,419,483 B1 * | 7/2002 | Adam et al. | 433/29 |
| 6,494,899 B1 * | 12/2002 | Griffin et al. | 607/88 |
| 6,602,074 B1 * | 8/2003 | Suh et al. | 433/228.1 |
| 2003/0172072 A1 * | 9/2003 | Smith | 707/10 |

FOREIGN PATENT DOCUMENTS

| | | | |
|---|---|---|---|
| DE | 37 32970 | | 6/1989 |
| EP | 0 780 104 | | 6/1997 |
| JP | 59-020812 | | 2/1984 |
| JP | 10-097896 | * | 4/1998 |
| JP | 2000-292857 | * | 10/2000 |
| WO | WO 99/22667 | | 5/1999 |
| WO | WO 01/15497 | | 3/2001 |

* cited by examiner

CURING LAMP APPARATUS GIVING OPERATING CONDITIONS WITH ELECTRONIC VOICE

CROSS-REFERENCE TO RELATED APPLICATION

The present application claims priority under 35 U.S.C. § 119(e) from U.S. Ser. No. 60/329,956, filed on Oct. 17, 2001. U.S. Ser. No. 60/329,956 was filed by at an inventor common to the present application, and is hereby incorporated by reference.

FIELD OF THE INVENTION

This invention relates to an apparatus and method for providing electronic voice information associated with an instrument, and more particularly, to an apparatus and method for providing electronic voice information associated with the performance and status of a dental curing instrument.

BACKGROUND

Light curing is a known technique in dentistry for curing, for example, composites and adhesives for the filling of root canals or fissures. Light cure restoratives are utilized throughout the dental care industry from dental maintenance to root canal restorations. Activation and polymerization of light cure restoratives must be carefully controlled. However, a means to inform a dental practitioner of an instrumentation measurement using a clear, audible language or tones appears to be lacking in the prior art.

Audible signals are known to be used in association with data items as displayed visually in a dental instrument, as in U.S. Pat. No. 4,968,252 to Creps. Yet, this present approach can lead a dental practitioner to confusion when surrounded by a multitude of such signals each prompting the practitioner for visual monitoring of the display in response to the audio signals. To view the display, the practitioner is thereby required to remove his or her vision from a field of action, resulting in a loss of time and focus on the dental task at hand.

Timing is a critical aspect of light curing in dental restorations. For dental fillings, a light cure restorative is typically placed in the apex of a tooth and activated with light. For root canal procedures, after a root canal is sealed, the remainder of the root canal is filled with light cure restorative and activated by light. An undesirable property of light-cured composite resin restorative materials is contraction during the curing process. For proper curing, curing light intensity must be carefully maintained, necessitating accurate tracking and monitoring. Dentists have learned through experience how to minimize the effects of contraction, and how to avoid open margins. Applying and curing small increments of the restorative material and accurate timing have been keys to minimizing these problems. However, managing accurate timing while practicing a dental procedure continues to present a substantial burden for dental practitioners.

SUMMARY OF THE INVENTION

These and other problems have been in a novel method and apparatus for operating a dental curing instrument. In a first embodiment of the present invention, the apparatus comprises a light sensor for sensing light output power density from a lamp of a curing light, a microcontroller, a programmed voice circuit and a speaker/transducer. The microcontroller comprises a plurality of analog to digital converters each for receiving an analog signal from one of the light sensor and the lamp for conversion to a digital number, a stored program and a memory for analyzing each digital number to produce an associated digital address, and an output for outputting the digital address. The programmed voice circuit, comprising a memory for storing voice messages and a processor for receiving a digital address output by the microcontroller, retrieves a voice message from a memory location identified by the digital number and outputs the voice message for reproduction by the speaker/transducer.

In accordance with a first method prescribed by the present invention, the apparatus of the first embodiment is operative to measure an output power density for the curing lamp and to play an audible voice message when the measured output power density exceeds a predetermined threshold. When the measured output density falls below the predetermined threshold, the apparatus of the first embodiment is operative to determine an input power being supplied to the curing lamp, and when the input power falls below a second predetermined threshold, to play an audible voice message indicating that the curing lamp should be replaced. The apparatus of the first embodiment is also operative to count a time of operation while the lamp is active, to store information indicative of a cumulative time of operation for the lamp, and to play an audible voice message announcing that an output power density for the lamp should be evaluated when the cumulative operating time reaches a third predetermined threshold.

BRIEF DESCRIPTION OF THE DRAWING

Further particular features of the invention will appear in the description, which will follow, of an embodiment taken by way of example and represented in the accompanying drawing, in which FIG. 1 provides a schematic diagram of a first embodiment of the present invention.

DETAILED DESCRIPTION OF THE PREFERRED EMBODIMENTS

A dental curing instrument is disclosed which has the functionality to verbalize the elapsed time of instrument usage as a curing lamp via electronically generated human speech in a chosen language output. For example, during the operation of the disclosed curing lamp, a user may need to know an amount of time that has elapsed. A known method of indicating time elapsed is an electronically generated beep (for example, every 10 seconds). However, such audible beeps can cause some confusion as to the nature of information being related and may distract a user of a curing apparatus from concentrating on the process of curing and caring for the needs of the patient. To solve this problem, elapsed time status is tracked by the disclosed invention and reported in an audible form immediately, allowing the user to focus his or her attention on the dental procedure.

The disclosed invention defines an electronic voice apparatus 1 comprising a programmed voice integrated circuit (IC) working together with a microcontroller that offers the user a measurement of the elapsed operating time beginning from the lamp's initial activation. Instead of using audible beeps, apparatus 1 offers the feature of electronically verbalizing the elapsed time in groups of seconds—"Ten seconds, Twenty seconds, . . . etc.", for example.

Advantageously, apparatus 1 can generate an electronic verbalization of required data in various languages selectable by the user. For example, at NYU Dental Center, dental students are present from all parts of the globe: Russia, India, Asia, the U.S., Pakistan, Israel, and so on. Thus, apparatus 1 offers the functionality to generate and electronically vocalize elapsed time and other information in various languages, from a novel customizable program choice of language selections, which can be utilized to treat dental care needs transcending language barriers by simply selecting a preferred language output. Thus, for example, the instrumentation can be shared by a multitude of students, with each able to easily select a language program choice.

Figure 1:
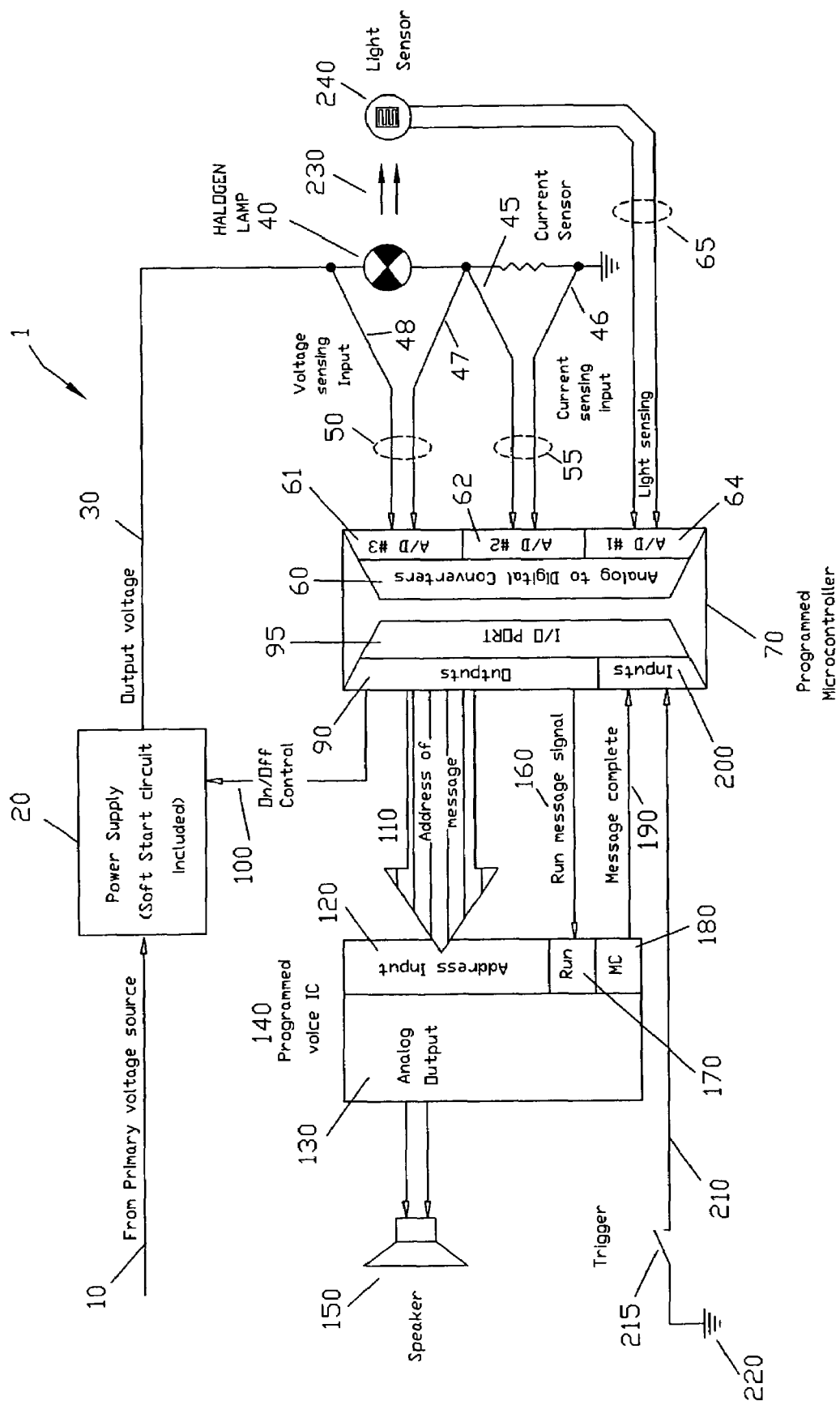
Figure 2A:
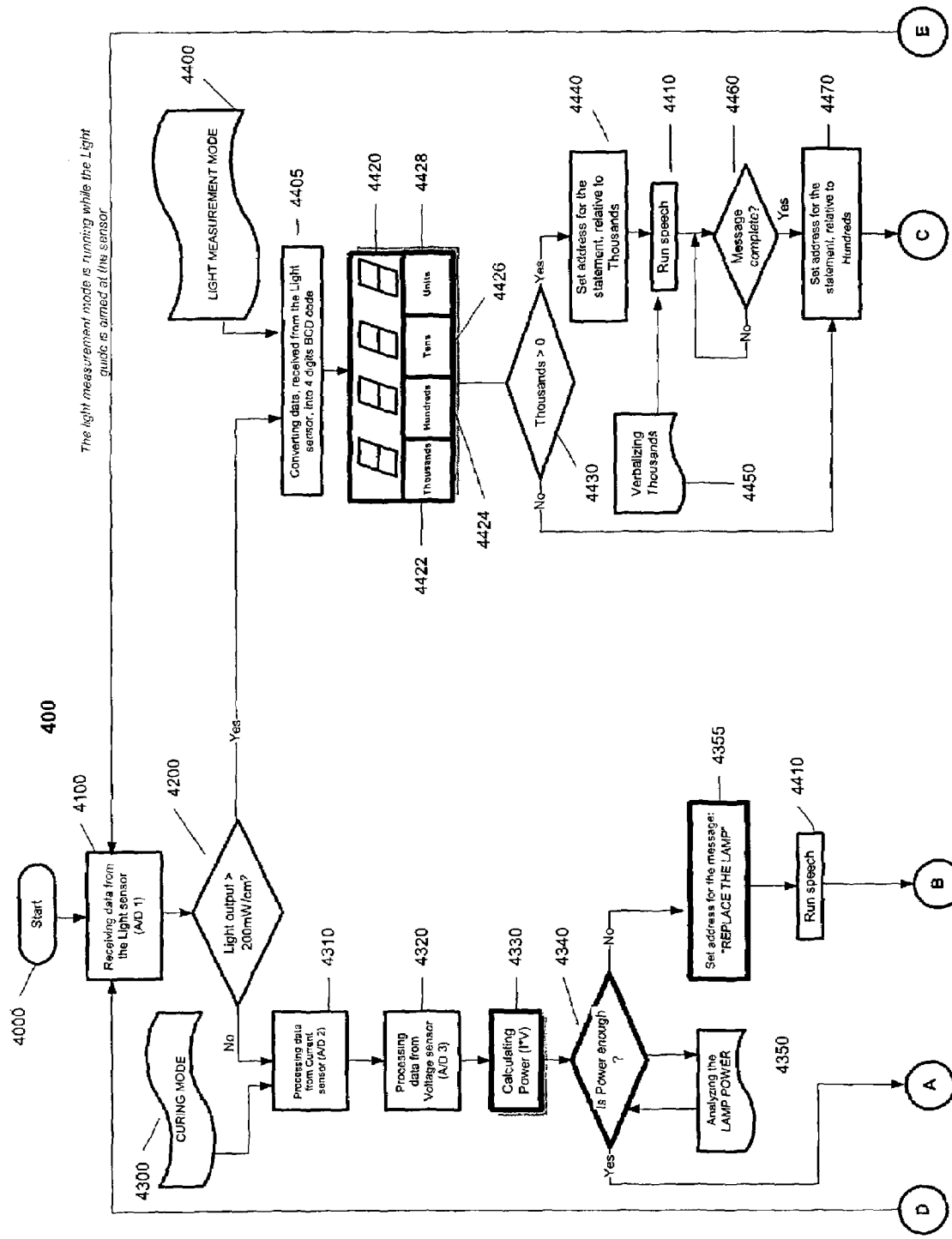
FIGS. 2A and 2B provide a process flow diagram for illustrating operation of the first embodiment.
Figure 2B:
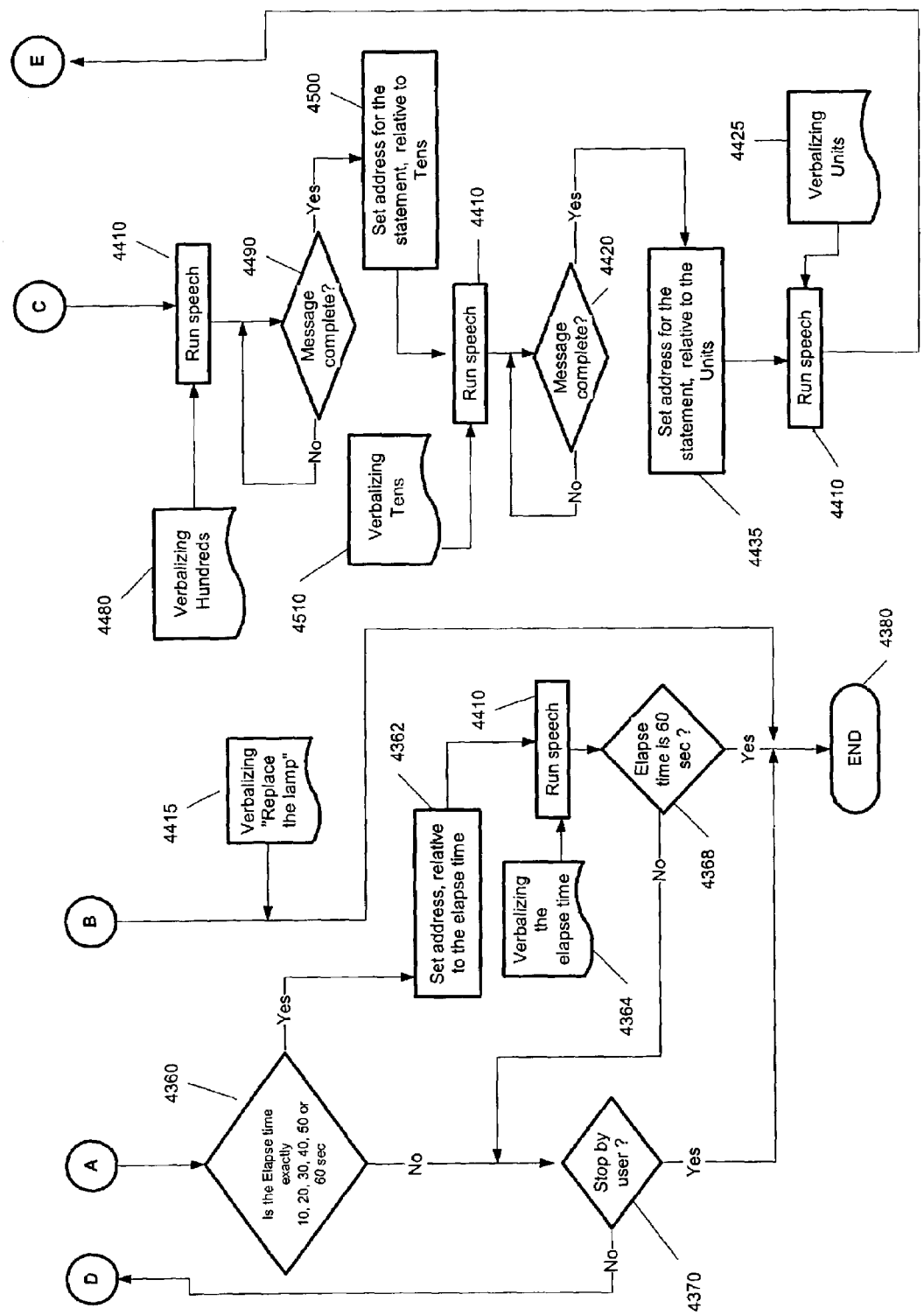

FIG. 1 and FIGS. 2A, 2B respectively illustrate apparatus 1 and operating method 400 for the present invention. To begin operation, as illustrated in FIG. 1, a lamp 40 is aimed so that light rays 230 impinge on light sensor 240. Lamp 40 is subjected to an output voltage 30 produced, for example, by a conventional power supply 20 fed by commercial voltage source 10.

Power supply 20, for example, may be switched on to provide output voltage 30 via a signal supplied by a control output 100 from outputs 90 at Input/Output Port 95 of microcontroller 70. Microcontroller 70 may be switched on, for example, by closing a trigger switch 215 to connect an input 210 to a system ground 220. Microcontroller 70 senses, for example, a voltage 65 produced by the light sensor 240 at an analog to digital converter (A/D 1) 64 in A/D section 60.

Operating method 400 begins at starting step 4000 as shown in FIG. 2A. Operating method 400 may be implemented, for example, by stored programs executed by microcontroller 70 and programmed voice IC 140 of FIG. 1. At step 4100 of FIG. 2A, microcontroller 70 determines whether a signal is being received at A/D section 60. At step 4200, a light output power density is determined, for example, based on the voltage 65 produced by light sensor 240.

If light output is not greater than 200 mW/cm$^2$ at step 4200, then a curing mode 4300 is executed by the microcontroller 70. A current 55 is detected at step 4310 via current sensing inputs 45, 46 at Analog/Digital Converter 2 (A/D 2) 62 of apparatus 1 as shown in FIG. 1. A voltage 50 is detected at step 4320 from voltage sensing inputs 47, 48 by the Analog/Digital Converter 3 (A/D 3) 61 of the programmed Microcontroller 70. Unit power is calculated as a product of current and voltage at step 4330. At step 4340, a decision is executed by the analysis routine 4350 to determine whether power is sufficient. If power is insufficient, then microcontroller 70 sets an address 110 associated with the voice message: "Replace the lamp" at step 4355, and runs an Electronic Speech output routine 4410 to cause address 110 to be output from outputs 90 of microcontroller 70 to an address input 120 of IC 140, and a run message signal 160 to be provided from outputs 90 of microcontroller 70 to run port 170 of IC 140. In response to outputs 90, IC 140 provides an analog output 130 to speaker/transducer 150 for vocalizing the voice message.

Returning to step 4200 of FIG. 2A, if the light output measurement of the unit is greater than 200 mW/cm$^2$, then Light Measurement Routine 4400 is initiated by the microcontroller 70. At step 4405, an analog signal is received from the Light sensor 240 via A/D controller 64 and converted into 4 digits of binary coded decimal (BCD) numbers. These numbers are used to represent the decimal digits 0–9. BCD code uses 4-bit binary coding at each decimal digit. To convert a BCD number into decimal, every 4-bits is converted into a decimal number. To convert a decimal number into BCD, each digit is simply converted into a 4-bit binary number, and is forwarded to a display (for example, a LED or digital read-out) providing digits for thousands, hundreds, tens and units as illustrated by positions 4422, 4424, 4426 and 4428 at step 4420.

At step 4430, if the decimal for thousands 4422 is greater than 0, an address is then set relative to thousands at step 4440. Electronic Embedded Speech routine 4410 is run, running electronic verbalization of the thousands measurement for the unit instrument at steps 4440, 4450 by microcontroller 70 communicating an appropriate address signal to the programmed voice IC 140 so that an associated voice message may be audibly reproduced by a speaker/transducer 150.

When the verbalizing of thousands measurement speech loop is complete at step 4460, the address statement is then set, relative to hundreds at steps 4470, 4480 as shown in FIGS. 2A, 2B. After the associated voice message is output by IC 140, IC 140 sends a message complete signal 190 from message port 180 to an input port 200 at Input/Output Port 95 of microcontroller 70. Speech routine 4410 is again run, running verbalizing of the hundreds data by the means previously described with reference to verbalizing thousands data.

When it is determined that the electronic verbalizing of hundreds speech loop is completed at step 4490, microcontroller 70 sets the address for the statement relative to the tens at steps 4500, 4510 and runs speech routine 4410. When the message is completely communicated at step 4420, then microcontoller 70 sets the address for the statement at step 4435, relative to the units of the data measurement provided by apparatus 1. A speech routine 4410 electronically verbalizes the units measurement at step 4425 from microcontroller 70 by signaling programmed voice IC 140, which outputs a voice signal to the speaker/transducer 150. When the output to speaker/transducer 150 is completed, operating method 400 returns to step 4100 of FIG. 2A.

An active lamp timer (not shown) is implemented by microcontroller 70, which supervises the real working time of the unit. The length of time the lamp is active is stored in a memory within the microcontroller 70. The counted time maybe conveniently stored into a memory of microcontroller 70, and is not erased, for example, when unit's electrical power is turned off. This feature helps to log real lamp usage, and can be configured to provide a schedule maintenance alert message for a user.

Over a lamp's lifetime, its light intensity decreases slowly, little by little. Most curing lamp instruments contain a powerful lamp, a spectrum filter, and a fiber optic tip, all of which are critically aligned. Any misalignment results in poor instrument operation. For this reason, it is very important to check the light intensity periodically to prevent insufficient curing. The disclosed invention provides this feature, such that the total amount of time that the lamp is used is stored in the memory of microcontroller 70. Apparatus 1 may accordingly notify the user by electronic "human" speech when it is time to check the lamp's intensity. This significantly lessens the burdening step of having to check instrument status.

Filament evaporation for lamp 40 of FIG. 1 causes the light output of lamp 40 to decrease over time. As a result, the filament's resistance increases, the current decreases, and the power lowers respectively. Light intensity decreases as power decreases. The present invention allows a user to continuously monitor the power applied to the lamp 40. Every lamp's resistance is unique. Therefore, even though a regulated voltage may be applied, power will be different with each individual lamp 40. The present invention allows a user to measure the power when a lamp has been installed or replaced, and store this value in the memory of miocro-controller 70.

Returning to FIG. 2A, to aid a user at each lamp activation of apparatus 1, a power measurement is initiated within curing process 4300. At step 4340, the measured power is compared with a stored ID value representing an initial value for lamp 40. If the measured power is out of a specified range, determined by the microcontroller 70 with reference to the initial ID value, an electronically generated voice message 4415 is made to "Replace the lamp" as indicated at steps 4355, 4410. Uniquely, apparatus 1 of FIG. 1 features functionality such that the light intensity never needs to be measured by a human operator to determine a replacement time for the lamp. Rather, apparatus 1 constantly monitors the lamp, and suggests replacement at an appropriate time for the ease and convenience of the user.

A lamp utilized in the present embodiment of apparatus 1 is a halogen-based lamp. Other lamp types which can be configured alone or in combination to produce like power densities are fully contemplated within scope of the present invention.

Returning to step 4340 of FIG. 2A, if the Power is determined to be sufficient at step 4350, then a decision is made at step 4360 to determine "Is the elapsed time exactly 10, 20, 30, 40, 50 or 60 sec?". If yes, then apparatus 1 steps to set an address relative to the elapsed time at step 4362, executes speech routine 4410, and electronically verbalizes the elapse time at step 4364. At step 4368, apparatus 1 determines "Is the elapsed time 60 sec?". If yes, then the routine of the unit ends at step 4380. If no, a check is made to determine whether apparatus 1 has been stopped by a user at step 4370. If yes, then method 400 ends at step 4380 of FIG. 2B. Otherwise, method 400 returns to step 4100 of FIG. 2A.

A display unit (not shown) may be optionally included in the dental curing instrument itself or on an adjacent control panel as an additional means for indicating data. The display unit may comprise segmental, LCD, LED or any other display means, and may be driven, for example, by the digital numbers provided by A/D section 60.

The foregoing describes the invention in terms of embodiments foreseen by the inventor for which an enabling description was available, notwithstanding that insubstantial modifications of the invention, not presently foreseen, may nonetheless equivalents thereto.

What is claimed is:

1. An apparatus for providing electronic voice information in a dental curing instrument, the apparatus comprising:
    a light sensor for sensing light output power density from a lamp of the curing instrument;
    a current sensing input for sensing current drawn by the curing lamp;
    a voltage sensing input for sensing voltage across the curing lamp;
    a microcontroller, the microcontroller comprising:
        a first analog to digital (A/D) converter operative to receive a first analog signal from the light sensor, and to convert the first analog signal to a first digital number,
        a second analog to digital (A/D) converter operative to receive a second analog signal from the current sensing, and to convert the second analog signal to a second digital number,
        a third analog to digital (A/D) converter operative to receive a third analog signal from the voltage sensing input, and to convert the third analog signal to a third digital number;
        a stored program and memory, the stored program and memory being operative to analyze one or more of the first, second and third digital numbers to produce a digital address; and
        an output for outputting the digital address;
    a programmed voice circuit comprising a memory for storing voice messages and a processor for receiving the digital address at an input, retrieving a voice message stored in the memory at the digital address, and outputting the voice message as an analog signal; and
    a transducer for receiving the output analog signal and outputting an audible voice message.

2. The apparatus of claim 1, wherein the microcontroller is programmable to select digital addresses for voice messages prepared in one of a plurality of languages.

3. The apparatus of claim 1, wherein the microcontroller is operative to output one or more of the first, second and third digital numbers for display on a visual display.

4. The apparatus of claim 3, wherein the visual display includes elements comprising at least one of light emitting diodes (LEDs) and liquid aystal display elements (LCDs).

5. The apparatus of claim 1, wherein the transducer includes an audio speaker.

6. A method for operating a curing light, the method comprising the steps of:
    determining an input power to a lamp in the curing light;
    when the determined input power falls below a predetermined threshold, playing an audible message indicating that the lamp should be replaced; and
    when the determined input power is at least equal to the predetermined threshold, the method further comprising the steps of:
        determining whether an elapsed time of operation matches a time reported by one of a plurality of predetermined time intervals; and
        playing an audible message announcing the elapsed time when a match is determined.

7. The method of claim 6, wherein when no match is found, the method comprising the steps of:
    determining whether operation continues by a user; and
    when operation continues, measuring an output power density for a lamp in the curing light.

8. A method for operating a curing light, the method comprising the steps of:
    determining an input power to a lamp in the curing light;
    when the determined input power falls below a predetermined threshold, the method further comprising the step of:
        playing an audible message indicating that the lamp should be replaced, and
    when the determined input power is at least equal to the predetermined threshold, the method further comprising the steps of:
        determining whether an elapsed time of operation matches a time reported by one of a plurality of predetermined time intervals, and
        playing an audible message announcing the elapsed time when a match is determined, and
        when the elapsed time exceeds a predetermined value, terminating the operation.

* * * * *